United States Patent
Bruchner et al.

(10) Patent No.: US 9,656,965 B2
(45) Date of Patent: May 23, 2017

(54) PROCEDURE FOR THE SYNTHESIS OF N-BENZYL-N-CYCLOPROPYL-1H-PYRAZOLE-4-CARBOXAMIDE DERIVATIVES

(71) Applicant: BAYER CROPSCIENCE AKTIENGESELLSCHAFT, Monheim am Rhein (DE)

(72) Inventors: Peter Bruchner, Krefeld (DE); Sergii Pazenok, Solingen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 14/916,496

(22) PCT Filed: Sep. 4, 2014

(86) PCT No.: PCT/EP2014/068838
§ 371 (c)(1),
(2) Date: Mar. 3, 2016

(87) PCT Pub. No.: WO2015/032859
PCT Pub. Date: Mar. 12, 2015

(65) Prior Publication Data
US 2016/0229808 A1   Aug. 11, 2016

(30) Foreign Application Priority Data
Sep. 5, 2013 (EP) .................................. 13356011

(51) Int. Cl.
*C07D 231/14* (2006.01)
*C07D 231/16* (2006.01)

(52) U.S. Cl.
CPC .......... *C07D 231/14* (2013.01); *C07D 231/16* (2013.01)

(58) Field of Classification Search
CPC .................................................... C07D 231/14
See application file for complete search history.

(56) References Cited

U.S. PATENT DOCUMENTS

| | | | |
|---|---|---|---|
| 8,772,266 B2 | 7/2014 | Bartels et al. | 514/63 |
| 8,927,581 B2 * | 1/2015 | Bennabi | C07D 401/12 514/341 |
| 9,398,767 B2 * | 7/2016 | Bartels | C07D 231/16 |
| 2014/0148411 A1 | 5/2014 | Bartels et al. | 514/63 |

FOREIGN PATENT DOCUMENTS

WO   WO 2010/130767 A2   11/2010

OTHER PUBLICATIONS

International Search Report issued Nov. 28, 2014 in corresponding International Application No. PCT/EP2014/068838.
Subhash Chandra Ghosh et al: "Iron-Catalyzed Efficient Synthesis of Amides from Aldehydes and Amine Hydrochloride Salts", Advanced Synthesis & Catalysis, vol. 354, No. 8, May 15, 2012 (May 15, 2012), pp. 1407-1412, XP055101856, DE, ISSN: 1615-4150, DOI: 10.1002/adsc.201200020.
Subhash Chandra Ghosh et al: "Copper-Catalyzed Oxidative Amidation of Aldehydes with Amine Salts: Synthesis of Primary, Secondary, and Tertiary Amides", The Journal of Organic Chemistry, vol. 77, No. 18, Aug. 16, 2012 (Aug. 16, 2012), pp. 8007-8015, XP055101861, US, ISSN: 0022-3263, DOI: 10.1021/jo301252c.
Istvan E. Marko et al: "Radical mediated oxidations in organic chemistry. 3. An efficient and versatile transformation of aldehydes into amides", Tetrahedron Letters, vol. 31, No. 49, 1990, pp. 7237-7240 XP055103614, GB, ISSN: 0040-4039, DOI: 10.1016/S0040-4039(00)97289-7.
Xiaoying Liu et al: "Direct oxidative amidation of aromatic aldehydes using aqueous hydrogen peroxide in continuous flow microreactor systems", Green Chemistry, vol. 14, No. 5, Mar. 13, 2012 (Mar. 13, 2012), pp. 1471-1474, XP055102177, GB, ISSN: 1463-9262, DOI: 10.1039/c2gc35078e.

* cited by examiner

*Primary Examiner* — Golam M M Shameem
(74) *Attorney, Agent, or Firm* — Morrison & Foerster LLP

(57) ABSTRACT

A new one-step process for the preparation of pyrazole carboxamide derivatives of the general formula (I)

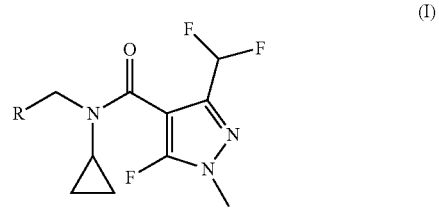

by reaction of 3-(difluoromethyl)-5-fluoro-1-methyl-1H-pyrazole-4-carbaldehyde with an amine or its salt.

12 Claims, No Drawings

PROCEDURE FOR THE SYNTHESIS OF N-BENZYL-N-CYCLOPROPYL-1H-PYRAZOLE-4-CARBOXAMIDE DERIVATIVES

CROSS-REFERENCE TO RELATED APPLICATION(S)

The present application is a 35 U.S.C. §371 national phase conversion of PCT/EP2014/068838 filed on Sep. 4, 2014, which claims priority of European Application No. 13356011.0 filed on Sep. 5, 2013. Applicants claim priority to each of the foregoing patent applications. The PCT International Application was published in the English language.

FIELD OF THE INVENTION

The present invention concerns the oxidative coupling of secondary benzylic amines with pyrazol carbaldehydes for the synthesis of pyrazole carboxamide derivatives. The synthesis of these compounds was described by WO 2010/130767 as a synthesis over two or more steps, starting from a pyrazol carbaldehyde via oxidation to the corresponding acid halogenide and its reaction with a benzylamine to the desired target compound in the final step.

BACKGROUND OF THE INVENTION

A synthesis of fluorinated pyrazolcarbaldehydes was described in patent WO 2011/061205. Secondary benzylic amines can be prepared as described in patent WO 2012/059585.

The direct oxidative coupling of aromatic aldehydes and secondary benzylic amines to the corresponding amide is described to some extent in literature. The group of Chen reported the oxidative amidation of various aldehydes with primary and secondary amine hydrochlorides in presence of base, an iron or copper catalyst and tert-Butylhydroperoxide as oxidant (*J. Org. Chem.* 2012, 77, 8007-8015; *Adv. Synth. Catal.* 2012, 354, 1407-1412). Pevarello et al. reported one example of oxidative coupling of an imidazothiadiazole carbaldehyde with N-methylbenzylamine in presence of tert-butylhydroperoxide in 29% yield (WO 2009/040552).

However, the oxidative coupling of pyrazolcarbaldehydes, let alone fluorinated pyrazolcarbaldehydes with secondary benzylic amines is not known in literature. In addition, most of the literature procedures for oxidative coupling of aldehyde with amines describe the use of excess aldehyde or amine, which decreases the economic efficiency of the reaction considerably.

SUMMARY OF THE INVENTION

Proceeding from this prior art it is the object of the present invention to provide an efficient method for the synthesis of pyrazole-4-carboxamides from a pyrazol carbaldehyde and secondary benzylic amines in only one step and without employing expensive transition metal catalysts or excess amounts of amine respectively aldehyde.

The present invention relates to a process for preparation of pyrazole carboxamides of the formula (I)

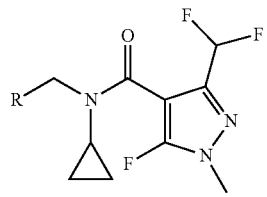

(I)

wherein R is selected from the list of 2-isopropylphenyl, 2-cyclopropylphenyl, 2-tert-butylphenyl, 5-chloro-2-ethylphenyl, 5-chloro-2-isopropylphenyl, 2-ethyl-5-fluorophenyl, 5-fluoro-2-isopropylphenyl, 2-cyclopropyl-5-fluorophenyl, 2-cyclopentyl-5-fluorophenyl, 2-fluoro-6-isopropylphenyl, 2-ethyl-5-methylphenyl, 2-isopropyl-5-methylphenyl, 2-cyclopropyl-5-methylphenyl, 2-tert-butyl-5-methylphenyl, 5-chloro-2-(trifluoromethyl)phenyl, 5-methyl-2-(trifluoromethyl)phenyl, 2-chloro-6-(trifluoromethyl)phenyl, 3-chloro-2-fluoro-6-(trifluoromethyl)phenyl and 2-ethyl-4,5-dimethylphenyl, by reaction of 3-(difluoromethyl)-5-fluoro-1-methyl-1H-pyrazole-4-carbaldehyde of the formula (II)

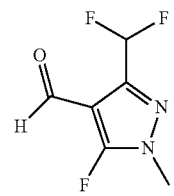

(II)

with an amine of the general formula (IIIa) or its salt of the general formula (IIIb)

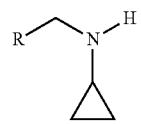

(IIIa)

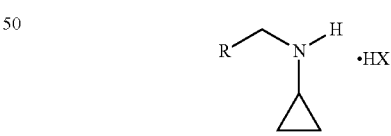

(IIIb)

wherein HX is selected from the list of HF, HCl, HBr, HJ; $H_2SO_4$, $HBF_4$, $CH_3SO_3H$, $CF_3SO_3H$, $CF_3CO_2H$ and R is as defined above, in presence of an oxidant and with a catalyst.

DETAILED DESCRIPTION OF THE INVENTION

In a particular embodiment of the invention, the amine derivative or its hydrochloride salt is of formula III-1

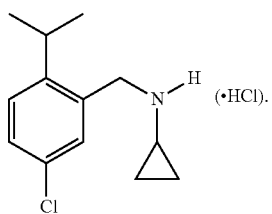

(III-1)

The process according to the invention is preferably used to prepare a compound of formula (I) selected from the group consisting of:
N-cyclopropyl-3-(difluoromethyl)-5-fluoro-N-(2-isopropylbenzyl)-1-methyl-1H-pyrazole-4-carboxamide,
N-cyclopropyl-N-(2-cyclopropylbenzyl)-3-(difluoromethyl)-5-fluoro-1-methyl-1H-pyrazole-4-carboxamide,
N-(2-tert-butylbenzyl)-N-cyclopropyl-3-(difluoromethyl)-5-fluoro-1-methyl-1H-pyrazole-4-carboxamide,
N-(5-chloro-2-ethylbenzyl)-N-cyclopropyl-3-(difluoromethyl)-5-fluoro-1-methyl-1H-pyrazole-4-carboxamide,
N-(5-chloro-2-isopropylbenzyl)-N-cyclopropyl-3-(difluoromethyl)-5-fluoro-1-methyl-1H-pyrazole-4-carboxamide,
N-cyclopropyl-3-(difluoromethyl)-N-(2-ethyl-5-fluorobenzyl)-5-fluoro-1-methyl-1H-pyrazole-4-carboxamide,
N-cyclopropyl-3-(difluoromethyl)-5-fluoro-N-(5-fluoro-2-isopropylbenzyl)-1-methyl-1H-pyrazole-4-carboxamide,
N-cyclopropyl-N-(2-cyclopropyl-5-fluorobenzyl)-3-(difluoromethyl)-5-fluoro-1-methyl-1H-pyrazole-4-carboxamide,
N-(2-cyclopentyl-5-fluorobenzyl)-N-cyclopropyl-3-(difluoromethyl)-5-fluoro-1-methyl-1H-pyrazole-4-carboxamide,
N-cyclopropyl-3-(difluoromethyl)-5-fluoro-N-(2-fluoro-6-isopropylbenzyl)-1-methyl-1H-pyrazole-4-carboxamide,
N-cyclopropyl-3-(difluoromethyl)-N-(2-ethyl-5-methylbenzyl)-5-fluoro-1-methyl-1H-pyrazole-4-carboxamide,
N-cyclopropyl-3-(difluoromethyl)-5-fluoro-N-(2-isopropyl-5-methylbenzyl)-1-methyl-1H-pyrazole-4-carboxamide,
N-cyclopropyl-N-(2-cyclopropyl-5-methylbenzyl)-3-(difluoromethyl)-5-fluoro-1-methyl-1H-pyrazole-4-carboxamide,
N-(2-tert-butyl-5-methylbenzyl)-N-cyclopropyl-3-(difluoromethyl)-5-fluoro-1-methyl-1H-pyrazole-4-carboxamide,
N-[5-chloro-2-(trifluoromethyl)benzyl]-N-cyclopropyl-3-(difluoromethyl)-5-fluoro-1-methyl-1H-pyrazole-4-carboxamide (compound A15),
N-cyclopropyl-3-(difluoromethyl)-5-fluoro-1-methyl-N-[5-methyl-2-(trifluoromethyl)benzyl]-1H-pyrazole-4-carboxamide (compound A16),
N-[2-chloro-6-(trifluoromethyl)benzyl]-N-cyclopropyl-3-(difluoromethyl)-5-fluoro-1-methyl-1H-pyrazole-4-carboxamide,
N-[3-chloro-2-fluoro-6-(trifluoromethyl)benzyl]-N-cyclopropyl-3-(difluoromethyl)-5-fluoro-1-methyl-1H-pyrazole-4-carboxamide.
N-cyclopropyl-3-(difluoromethyl)-N-(2-ethyl-4,5-dimethylbenzyl)-5-fluoro-1-methyl-1H-pyrazole-4-carboxamide,
and N-cyclopropyl-3-(difluoromethyl)-5-fluoro-N-(2-isopropylbenzyl)-1-methyl-1H-pyrazole-4-carbothio-amide.

Process Description

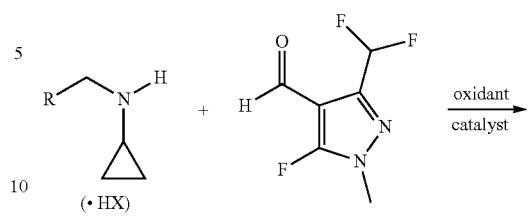

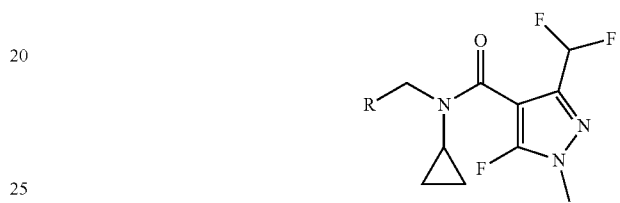

The oxidative amidation step is performed in the presence of an oxidant, a catalyst and optionally a base.

The ratio between amine III and aldehyde II can vary from 1.5:1 to 1:0.5, preferably from 1.2:1 to 1:0.5, most preferably from 1.2:1 to 1:1.

The oxidant is selected from sodium hypochlorite, cumenehydroperoxide, tert-butylhydroperoxide, hydrogenperoxide, sulfurylchloride, N-bromosucinimide, N-chlorosuccinimide, meta-chloroperbenzoic acid, bromine; preferred are sulfurylchloride, tert-butylhydroperoxide and cumenehydroperoxide, most preferred are tert-butylhydroperoxide and cumenehydroperoxide.

The amount of the oxidant can vary from 0.5-5 equivalents; preferably from 1-2.5 equivalents, more preferably from 1.5-2.5

If amine salt IIIb is employed in the reaction, then a base is used for this process and is either an organic or inorganic base. A single compound or a mixture is selected from $Na_2CO_3$, NaOH, $K_2CO_3$, $CaCO_3$, CaO, $Ca(OH)_2$ or an organic base such as $Et_3N$; preferred are $Na_2CO_3$; $K_2CO_3$, $CaCO_3$, especially preferred is $CaCO_3$.

The catalyst is selected from $CuSO_4*5H_2O$, $FeSO_4*7H_2O$, $CoSO_4*7H_2O$, $NiSO_4$, preferred is $CuSO_4*5H_2O$, $FeSO_4*7H_2O$, especially preferred is $FeSO_4*7H_2O$.

The reaction is performed in the presence of a solvent, which can be selected from toluene, methanol, valeronitrile, acetonitrile, N,N-dimethylformamide, water, tetrachloromethane, chloroform, chlorobenzene, preferably valeronitrile and acetonitrile, more preferably acetonitrile.

The reaction time of the process according to the invention is generally not of critical importance and can depend on the reaction volume; preferably it is within the range of 3 to 12 h.

The temperature of the process according to the invention is ranging from 0° C. to 150° C.; preferably from 20° C. to 120° C., more preferably from 60° C. to 90° C.

EXAMPLES

Example 1

N-(5-chloro-2-isopropylbenzyl)-N-cyclopropyl-3-(difluoromethyl)-5-fluoro-1-methyl-1H-pyrazole-4-carboxamide

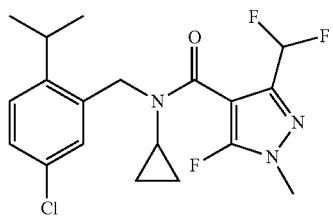 [SMILES: CC(C)c1ccc(Cl)cc1CN(C(=O)c1c(C(F)F)nn(C)c1F)C1CC1]

To a mixture of $FeSO_4*7H_2O$ (0.55 mmol, 0.15 g), $CaCO_3$ (5.63 mmol, 0.563 g) and N-(5-chloro-2-isopropylbenzyl)cyclopropylamine hydrochloride (2.8 mmol, 0.725 g) in acetonitrile (2 g) was added 3-(difluoromethyl)-5-fluoro-1-methyl-1H-pyrazole-4-carbaldehyde (2.8 mmol, 0.5 g). The suspension was heated to 60° C. and a solution of t-Butylhydroperoxide (7.7 mmol, 0.69 g) in acetonitrile (2 g) was added over 10 hours. The resulting mixture was treated with 1M hydrochloric acid, extracted with dichloromethane, the organic layer washed with sodiumbisulfit solution and concentrated in vacuo to obtain the crude product (60% purity by quantitative LC, 1.02 g, 57% theoretical yield).

$^1$H NMR (DMSO-d6, 600 MHz, 25° C.): δ=m7.38-7.37 (m, 1H), 7.34-7.32 (m, 1H), 7.20 (m, 1H), 6.99 (t, 1H, $CF_2H$, $J_{H-F}$=54 Hz), 4.69 (s, 2H), 3.80 (s, 3H, N—$CH_3$), 3.18-3.10 (br m, 1H), 2.63-2.48 (br m, 1H), 1.18 (d, 6H, J=6.6 Hz), 0.67-0.63 (m, 4H) ppm.

Example 2

A Further Procedure for Synthesis of N-(5-chloro-2-isopropylbenzyl)-N-cyclopropyl-3-(difluoromethyl)-5-fluoro-1-methyl-1H-pyrazole-4-carboxamide To a mixture of $FeSO_4*7H_2O$ (0.26 mmol, 0.073 g), $CaCO_3$ (0.53 mmol, 0.053 g) and N-(5-chloro-2-isopropylbenzyl)cyclopropylamine hydrochloride (0.94 mmol, 0.167 g) in acetonitrile (0.9 g) was added 3-(difluoromethyl)-5-fluoro-1-methyl-1H-pyrazole-4-carbaldehyde (0.56 mmol, 0.1 g). The suspension was heated to 60° C. and aqueous NaOCl solution (13 wt-%; 0.58 mmol, 0.331 g) was added. The resulting mixture was stirred until LCMS of the crude reaction indicated the formation of the target product.

Example 3

A Further Procedure for Synthesis of N-(5-chloro-2-isopropylbenzyl)-N-cyclopropyl-3-(difluoromethyl)-5-fluoro-1-methyl-1H-pyrazole-4-carboxamide The procedure was followed as described in Example 2 but with aqueous $H_2O_2$ solution (30 wt-%) instead of NaOCl as the oxidant.

Example 4

A Further Procedure for Synthesis of N-(5-chloro-2-isopropylbenzyl)-N-cyclopropyl-3-(difluoromethyl)-5-fluoro-1-methyl-1H-pyrazole-4-carboxamide The procedure was followed as described in Example 1 but with N,N-Dimethylformamide as solvent instead of acetonitrile.

Example 5

A Further Procedure for Synthesis of N-(5-chloro-2-isopropylbenzyl)-N-cyclopropyl-3-(difluoromethyl)-5-fluoro-1-methyl-1H-pyrazole-4-carboxamide The procedure was followed as described in Example 1 but with methanol as solvent instead of acetonitrile.

Example 6

A Further Procedure for Synthesis of N-(5-chloro-2-isopropylbenzyl)-N-cyclopropyl-3-(difluoromethyl)-5-fluoro-1-methyl-1H-pyrazole-4-carboxamide The procedure was followed as described in Example 1 but with toluene as solvent instead of acetonitrile.

Example 7

A Further Procedure for Synthesis of N-(5-chloro-2-isopropylbenzyl)-N-cyclopropyl-3-(difluoromethyl)-5-fluoro-1-methyl-1H-pyrazole-4-carboxamide To a mixture of $FeSO_4*7H_2O$ (0.26 mmol, 0.074 g), $CaCO_3$ (10.7 mmol, 1.072 g) and N-(5-chloro-2-isopropylbenzyl)cyclopropylamine hydrochloride (6.0 mmol, 1.564 g) in acetonitrile (4 g) was added 3-(difluoromethyl)-5-fluoro-1-methyl-1H-pyrazole-4-carbaldehyde (5.6 mmol, 1 g). The suspension was heated to 60° C. and a solution of cumenehydroperoxide (8.7 mmol, 1.325 g) in acetonitrile (3.5 g) was added over 5 hours. The resulting mixture was treated with sodiumbisulfit and extracted with dichloromethane. The resulting organic layer was concentrated in vacuo to obtain the crude product (24% purity by quantitative LC, 2.3 g, 26%).

Example 8

A Further Procedure for Synthesis of N-(5-chloro-2-isopropylbenzyl)-N-cyclopropyl-3-(difluoromethyl)-5-fluoro-1-methyl-1H-pyrazole-4-carboxamide To a mixture of $FeSO_4*7H_2O$ (0.025 mmol, 0.007 g), $CaCO_3$ (0.053 mmol, 0.053 g) and N-(5-chloro-2-isopropylbenzyl)cyclopropylamine hydrochloride (0.94 mmol, 0.167 g) in acetonitrile (0.9 g) was added 3-(difluoromethyl)-5-fluoro-1-methyl-1H-pyrazole-4-carbaldehyde (0.56 mmol, 0.1 g). The suspension was heated to 60° C. and a solution of t-Butylhydroperoxide (0.57 mmol, 0.074 g) was added. The resulting mixture was stirred until LCMS of the crude reaction indicated the formation of the target product.

The invention claimed is:

1. Process for the synthesis of pyrazolecarboxamide of the formula (I)

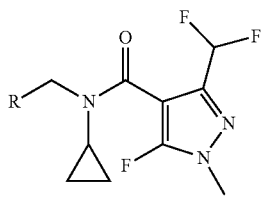

(I)

wherein R is selected from the list of 2-isopropylphenyl, 2-cyclopropylphenyl, 2-tert-butylphenyl, 5-chloro-2-ethylphenyl, 5-chloro-2-isopropylphenyl, 2-ethyl-5-fluorophenyl, 5-fluoro-2-isopropylphenyl, 2-cyclopropyl-5-fluorophenyl, 2-cyclopentyl-5-fluorophenyl, 2-fluoro-6-isopropylphenyl, 2-ethyl-5-methylphenyl, 2-isopropyl-5-methylphenyl, 2-cyclopropyl-5-methylphenyl, 2-tert-butyl-5-methylphenyl, 5-chloro-2-(trifluoromethyl)phenyl, 5-methyl-2-(trifluoromethyl)phenyl, 2-chloro-6-(trifluoromethyl)phenyl, 3-chloro-2-fluoro-6-(trifluoromethyl)phenyl and 2-ethyl-4,5-dimethylphenyl, by reaction of 3-(difluoromethyl)-5-fluoro-1-methyl-1H-pyrazole-4-carbaldehyde of the general formula (II)

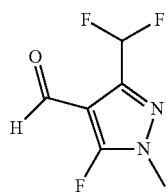

(II)

with an amine of the general formula (IIIa) or its salt of the general formula (IIIb)

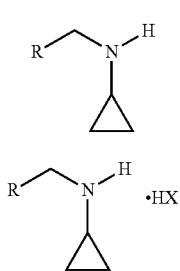

(IIIa)

(IIIb)

wherein HX is selected from the list of HF, HCl, HBr, HJ; H$_2$SO$_4$, HBF$_4$, CH$_3$SO$_3$H, CF$_3$SO$_3$H, CF$_3$CO$_2$H and R is as defined above, in presence of an oxidant and with a catalyst.

2. Process according to claim 1, wherein the amine derivative or its hydrochloride salt are of formula III-1

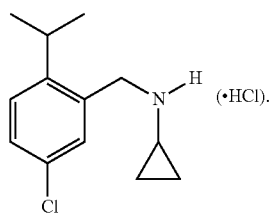

(III-1)

3. Process according to claim 1 for preparation of a carboxamide derivative selected from the group consisting of:

N-cyclopropyl-3-(difluoromethyl)-5-fluoro-N-(2-isopropylbenzyl)-1-methyl-1H-pyrazole-4-carboxamide,
N-cyclopropyl-N-(2-cyclopropylbenzyl)-3-(difluoromethyl)-5-fluoro-1-methyl-1H-pyrazole-4-carboxamide,
N-(2-tert-butylbenzyl)-N-cyclopropyl-3-(difluoromethyl)-5-fluoro-1-methyl-1H-pyrazole-4-carboxamide,
N-(5-chloro-2-ethylbenzyl)-N-cyclopropyl-3-(difluoromethyl)-5-fluoro-1-methyl-1H-pyrazole-4-carboxamide,
N-(5-chloro-2-isopropylbenzyl)-N-cyclopropyl-3-(difluoromethyl)-5-fluoro-1-methyl-1H-pyrazole-4-carboxamide,
N-cyclopropyl-3-(difluoromethyl)-N-(2-ethyl-5-fluorobenzyl)-5-fluoro-1-methyl-1H-pyrazole-4-carboxamide,
N-cyclopropyl-3-(difluoromethyl)-5-fluoro-N-(5-fluoro-2-isopropylbenzyl)-1-methyl-1H-pyrazole-4-carboxamide,
N-cyclopropyl-N-(2-cyclopropyl-5-fluorobenzyl)-3-(difluoromethyl)-5-fluoro-1-methyl-1H-pyrazole-4-carboxamide,
N-(2-cyclopentyl-5-fluorobenzyl)-N-cyclopropyl-3-(difluoromethyl)-5-fluoro-1-methyl-1H-pyrazole-4-carboxamide,
N-cyclopropyl-3-(difluoromethyl)-5-fluoro-N-(2-fluoro-6-isopropylbenzyl)-1-methyl-1H-pyrazole-4-carboxamide,
N-cyclopropyl-3-(difluoromethyl)-N-(2-ethyl-5-methylbenzyl)-5-fluoro-1-methyl-1H-pyrazole-4-carboxamide,
N-cyclopropyl-3-(difluoromethyl)-5-fluoro-N-(2-isopropyl-5-methylbenzyl)-1-methyl-1H-pyrazole-4-carboxamide,
N-cyclopropyl-N-(2-cyclopropyl-5-methylbenzyl)-3-(difluoromethyl)-5-fluoro-1-methyl-1H-pyrazole-4-carboxamide,
N-(2-tert-butyl-5-methylbenzyl)-N-cyclopropyl-3-(difluoromethyl)-5-fluoro-1-methyl-1H-pyrazole-4-carboxamide,
N-[5-chloro-2-(trifluoromethyl)benzyl]-N-cyclopropyl-3-(difluoromethyl)-5-fluoro-1-methyl-1H-pyrazole-4-carboxamide,
N-cyclopropyl-3-(difluoromethyl)-5-fluoro-1-methyl-N-[5-methyl-2-(trifluoromethyl)benzyl]-1H-pyrazole-4-carboxamide,
N-[2-chloro-6-(trifluoromethyl)benzyl]-N-cyclopropyl-3-(difluoromethyl)-5-fluoro-1-methyl-1H-pyrazole-4-carboxamide,
N-[3-chloro-2-fluoro-6-(trifluoromethyl)benzyl]-N-cyclopropyl-3-(difluoromethyl)-5-fluoro-1-methyl-1H-pyrazole-4-carboxamide,
N-cyclopropyl-3-(difluoromethyl)-N-(2-ethyl-4,5-dimethylbenzyl)-5-fluoro-1-methyl-1H-pyrazole-4-carboxamide, and N-cyclopropyl-3-(difluoromethyl)-5-fluoro-N-(2-isopropylbenzyl)-1-methyl-1H-pyrazole-4-carbothioamide.

4. Process according to claim 1, wherein the oxidative step is performed in presence of a base.

5. Process according to claim 4 wherein the base is selected from the group consisting of $Na_2CO_3$, NaOH, $K_2CO_3$, $CaCO_3$, CaO, $Ca(OH)_2$, $Et_3N$ and mixture thereof.

6. Process according to claim 4 wherein the base is $CaCO_3$.

7. Process according to claim 1, wherein the catalyst is selected from the group consisting of $CuSO_4*5H_2O$, $FeSO_4*7H_2O$, $CoSO_4*7H_2O$, and $NiSO_4$.

8. Process according to claim 7, wherein the catalyst is $FeSO_4*7H_2O$.

9. Process according to claim 1, wherein the oxidant is selected from the group consisting of sodium hypochlorite, cumenehydroperoxide, tert-butylhydroperoxide, hydrogenperoxide, sulfwylchloride, N-bromosucinimide, N-chlorosuccinimide, meta-chloroperbenzoic acid, and bromine.

10. Process according to claim 9 wherein the oxidant is selected from cumenehydroperoxide or tert-butylhydroperoxide.

11. Process according to claim 1, wherein the reaction is performed in presence of a solvent selected from toluene, methanol, valeronitrile, acetonitrile, N,N-dimethylformamide, water, tetrachloromethane, chloroform, or chlorobenzene.

12. Process according to claim 11 wherein the solvent is acetonitrile.

* * * * *